(12) United States Patent
Caskey et al.

(10) Patent No.: US 10,744,492 B2
(45) Date of Patent: Aug. 18, 2020

(54) ADSORBENT FOR CONTAMINANT REMOVAL FROM C4 HYDROCARBONS

(71) Applicant: UOP LLC, Des Plaines, IL (US)

(72) Inventors: Stephen R. Caskey, Lake Villa, IL (US); Munish Kumar Sharma, New Delhi (IN); Jayant K. Gorawara, Buffalo Grove, IL (US); Pijus Kanti Roy, New Delhi (IN); Frank S. Modica, Naperville, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 15/802,766

(22) Filed: Nov. 3, 2017

(65) Prior Publication Data

US 2020/0023341 A1    Jan. 23, 2020

(51) Int. Cl.
*B01J 29/08*    (2006.01)
*B01D 15/00*    (2006.01)

(52) U.S. Cl.
CPC ............ *B01J 29/082* (2013.01); *B01D 15/00* (2013.01); *B01D 2253/1085* (2013.01); *C10G 2300/104* (2013.01); *C10G 2300/1025* (2013.01)

(58) Field of Classification Search
None
See application file for complete search history.

(56) References Cited

U.S. PATENT DOCUMENTS

| 3,402,996 | A | * | 9/1968 | Maher ................... B01J 20/186 502/79 |
|---|---|---|---|---|
| 3,992,471 | A | | 11/1976 | Priegnitz |
| 6,423,658 | B1 | | 7/2002 | Thonnelier et al. |
| 7,326,821 | B2 | * | 2/2008 | Risch ........................ C07C 7/12 585/639 |
| 7,651,550 | B2 | | 1/2010 | Hawes et al. |
| 8,710,285 | B1 | | 4/2014 | Nicholas et al. |
| 8,888,993 | B2 | | 11/2014 | Verma et al. |
| 9,024,104 | B2 | | 5/2015 | Riley et al. |

(Continued)

FOREIGN PATENT DOCUMENTS

| EP | 639400 A1 | 2/1995 |
|---|---|---|
| EP | 1080056 B1 | 8/2004 |

(Continued)

OTHER PUBLICATIONS

Wolfe, Addition of Aliphatic Amines ((AA)) to Montmorillonite to Improve Its Adsorption Capacity for Organic Pollutants in Aqueous Solution, Iowa State Univ., Diss. (1981) 90P (Abstr.) Diss. Abstr. Int. B V42 N.11 4515-B (May 1982), 1981.

(Continued)

*Primary Examiner* — Anita Nassiri-Motlagh

(57) ABSTRACT

A process is provided for removing contaminants from olefin containing $C_4$ streams. The streams are contacted with an X based zeolite adsorbent comprising greater than 88% X zeolite at a $SiO_2/Al_2O_3$ ratio of less than 2.5 and an alkali metal salt present in excess of an amount required to achieve full exchange of cation sites on the X based zeolite. The resulting alkali oxide on a volatile free basis is less than 1% (by mass) of the X based adsorbent. The contaminants that are removed include sulfur, oxygenate, and nitrogen based contaminants.

20 Claims, 6 Drawing Sheets

(56) References Cited

U.S. PATENT DOCUMENTS

| | | | |
|---|---|---|---|
| 9,175,230 B2 | 11/2015 | Long et al. | |
| 2011/0104494 A1* | 5/2011 | Brandt | B01D 53/02 |
| | | | 428/402 |
| 2014/0364672 A1 | 12/2014 | Bracco et al. | |
| 2017/0050903 A1 | 2/2017 | Dolan | |

FOREIGN PATENT DOCUMENTS

| | | |
|---|---|---|
| EP | 1148025 B1 | 8/2007 |
| KR | 20120108542 A | 10/2012 |
| WO | 2015157429 A1 | 10/2015 |

OTHER PUBLICATIONS

Vignola et.al., Zeolites in a permeable reactive barrier (PRB): One-year of field experience in a refinery groundwater Part 2: Zeolite characterization, Chemical Engineering Journal, v 178, p. 210-216, Dec. 15, 2011.

Sharma, et.al., Desorption of Organic Liquids From Micro- and Mesoporous Adsorbents, Z. Phys. Chem. (Wiesbaden) V130 N.Part 2 241-45 (1982), v 130, n Part 2, p. 241-245, 1982.

Xu et.al., Preparation and characterization of novel CO2 molecular basket adsorbents based on polymer-modified rnesoporous molecular sieve MCM-41, Microporous and Mesoporous Materials, v 62, n 1/2, p. 29-45, Aug. 14, 2003.

International Search Report and Written Opinion from corresponding PCT application No. PCT/US2018/058344, dated Feb. 14, 2019.

* cited by examiner

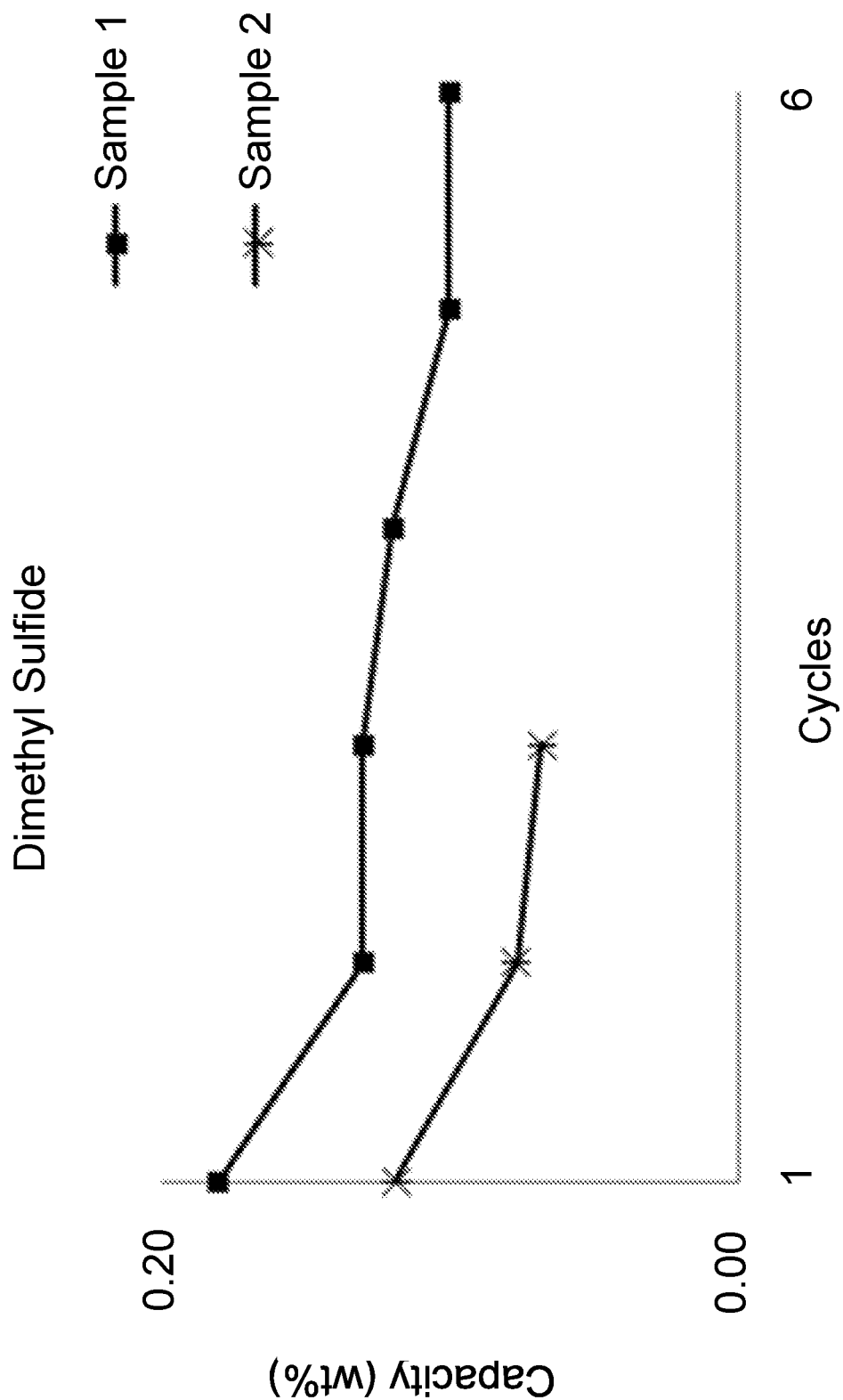

ADSORBENT FOR CONTAMINANT REMOVAL FROM C4 HYDROCARBONS

BACKGROUND OF THE INVENTION

The increased use of ethane from shale gas supplanting naphtha for steam cracking has reduced the quantity of $C_4$ produced for petrochemical and other applications. This has driven the increased demand for $C_4$ feedstocks derived from refineries which are increasingly being used to supplement traditional steam cracker feeds for petrochemical applications in particular. Standard adsorbents such as 13x zeolites offer insufficient capacity and poor regenerability in highly contaminated light hydrocarbon feedstocks such as those from refineries especially when olefins are present even in concentrations as low as 0.1%. Higher capacity and improved regenerability adsorbents are needed to handle these more contaminated refinery C4 feeds. Standard adsorbents suffer from poor regenerability in difficult, highly contaminated feed streams in particular where oxygenates and olefins are present. A commonly held belief in the industry is that the presence of olefins in the feed stream and particularly adsorbed olefins during regeneration are the main source of coking for adsorbents in process industry applications. However, it has been discovered that oxygenates are significant contributors to coking and potentially more detrimental than olefins. Multiple pathways for coke are present in these types of feed streams: acid catalyzed olefin oligomerization reactivity and acid or base catalyzed Aldol condensation reactivity of oxygenates, specifically carbonyls. High levels of coking are typically directly attributable to poor regenerative capacity. Therefore, an optimal adsorbent is needed to minimize the level of coking, not just toward acid catalyzed olefin oligomerization, but also toward acid and base catalyzed Aldol condensation reactions.

The adsorbent of the present invention provides 15-50% higher regenerative capacities (compared to prior art adsorbents) for a wide variety of nitrogen, oxygenate, and sulfur compounds from contaminated light hydrocarbons such as C4s and especially in olefin containing streams. In addition to higher zeolite content and higher cation density, this adsorbent offers improved access to adsorption sites through higher microporosity and larger macropores. The improved macroporosity provides additional space for carbon buildup without substantively impacting diffusivity and capacity.

SUMMARY OF THE INVENTION

The invention provides a process for removing contaminants from olefin containing $C_4$ streams comprising contacting said olefin containing $C_4$ streams with an X-based zeolite adsorbent comprising more than 88% X zeolite at a $SiO_2/Al_2O_3$ ratio of less than 2.5 and an alkali metal salt present in excess of an amount required to achieve full exchange of cation sites on the X-based zeolite. The resulting alkali oxide on a volatile free basis is less than 1% (by mass) of the X-based adsorbent. The contaminants that are removed include sulfur, oxygenate, and nitrogen based contaminants. The X-based zeolite adsorbent exhibits a maximum on a log differential specific intrusion volume as measured by Hg porosimetry at a pore diameter of greater than 3000 Angstroms. The X-based zeolite adsorbent may exhibit a maximum on the log differential specific intrusion volume as measured by Hg Porosimetry at a pore diameter between 3000 and 9000 Angstroms or between 3000 and 6000 Angstroms as shown in FIG. 1 in a Log Scale for Samples 1 and 2.

The operating conditions may include a LHSV from 1-15 $hr^{-1}$, adsorption temperature of 15-70° C. and a pressure of 100-550 psig. In an embodiment of the invention, the X-based zeolite adsorbent is dried in two drying stages comprising a first zone of about 204° C. (400° F.) and a second zone of about 343° C. (650° F.). In another embodiment of the invention, the X-based zeolite adsorbent is dried in three drying stages comprising a first zone of about 385° C. (725° F.), a second zone of about 538° C. (1000° F.). and a third zone of about 576° C. (1070° F.). The X-based zeolite adsorbent may further comprise a binder.

More specifically, sulfur contaminants that are removed may include mercaptans, disulfides, sulfides and mixtures thereof. The oxygenate contaminants may include alcohols, ethers, peroxides, carbonyl compounds and mixtures thereof. The nitrogen contaminants that are removed may include nitriles, amines and mixtures thereof.

In an embodiment of the invention, the $SiO_2/Al_2O_3$ ratio in the X-based zeolite adsorbent is about 2.1. The alkali metal salt may be selected from sodium, potassium, rubidium, cesium salts of acetate, carbonate, carboxylate and polyacrylic acid. Preferably, the alkali metal salt is selected from sodium salts of acetate, carbonates, carboxylates and polyacrylic acid. The X-based zeolite adsorbent has a micropore volume of greater than 0.28 g/cc measured by a t-plot method. Preferably, the X based zeolite adsorbent has a micropore volume between 0.28 to 0.30 g/cc as measured by the t-plot method. The X-based zeolite may be regenerated in a thermal swing adsorption process at a temperature from about 250° C. and 300° C. in a heated gas. The process is able to remove contaminants to a level that less than 1 wppm of the contaminants remain in the olefin containing $C_4$ streams after contact with the X-based zeolite of the present invention. In addition, it has been found that the X-based zeolite after use to remove contaminants has a reduced level of coke buildup.

BRIEF DESCRIPTION OF THE DRAWINGS

FIG. 3C shows dimethyl sulfide regenerability curve demonstrating higher capacity and better regenerability using new adsorbent.

DETAILED DESCRIPTION OF THE INVENTION

The invention provides a process for removing contaminants from olefin containing $C_4$ streams. The process comprises contacting an olefin containing $C_4$ stream with an X-based zeolite adsorbent comprising more than 88% X zeolite having a $SiO_2/Al_2O_3$ ratio of less than 2.5. The X-based zeolite adsorbent also contains an alkali metal salt present in excess of an amount required to achieve full exchange of cation sites on said X based zeolite wherein a resulting alkali oxide on a volatile free basis is less than 1% (by mass) of the X based adsorbent.

Figure 1:
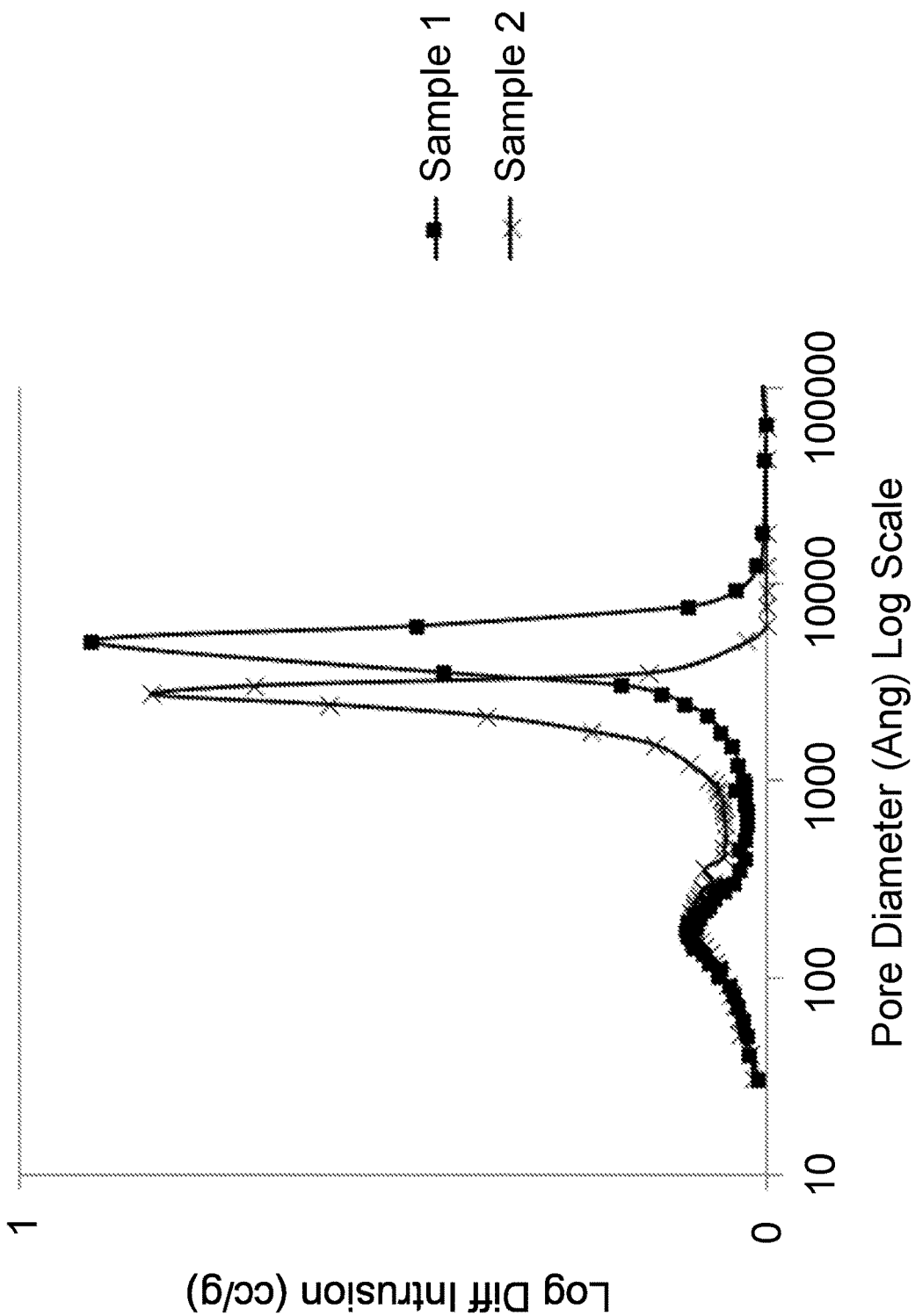
FIG. 1 shows mercury porosimetry describing pore volume (cc/g) as a function of pore diameter (nm) for new adsorbent compared to old adsorbent.
Figure 2:
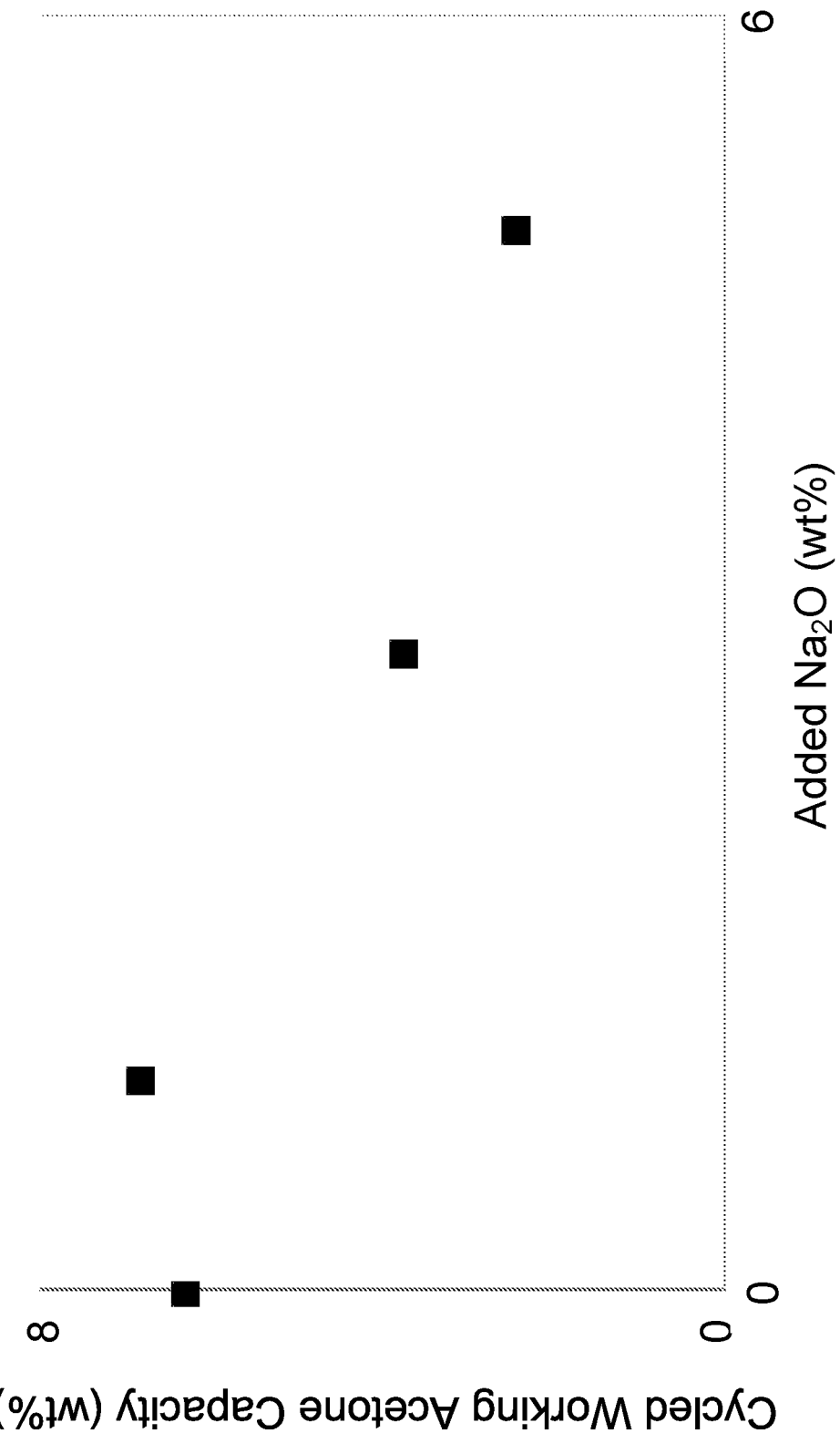
FIG. 2 shows cycled capacity of acetone on adsorbent samples with varying amounts of added Na2O.

The adsorbent of the present invention in an embodiment is a 90% 2.1× adsorbent bound with attapulgite clay. Dispex NA is used as dispersing agent in the forming process. A mixing process such as Nauta forming is used for generating adsorbent beads. The material is then dried and calcined under specific conditions. The adsorbent of this invention offers higher zeolite content, higher cation density, higher microporosity, and improved macroporosity. These aspects allow the adsorbent to provide higher capacity and improved regenerability in spite of similar rates of processing and levels of coking. In the past, higher macroporosity has sometimes been thought of as an undesirable condition in terms of zeolite adsorbent materials because it tends to lower the packed density of the adsorbent thus lowering the available zeolite in a given volume. However, this adsorbent allows improved access to the adsorption sites due to larger macropores which can handle higher levels of coking in this difficult, highly contaminated feed stream. This new adsorbent provides an optimal balance of acidic and basic functions to limit coking and improve regenerability in oxygenate and olefinic containing feed streams. The adsorbent minimizes the base catalyzed Aldol condensation reactivity which has proven to be particularly detrimental while not substantially increasing the acid catalyzed olefin oligomerization activity. The adsorbent offers high zeolite content (>85%) to minimize acidic reactivity that may be present in the binder. The adsorbent has optimized additives, drying, and calcination conditions to find the right balance of acidity and basicity. Optionally the adsorbent could be doped with a small amount (0-1%) of additional sodium oxide typically in the form of sodium acetate to further refine the acid/base properties as shown in FIG. 2. FIG. 2 shows the cycled capacity of acetone in wt % on adsorbent samples with varying amounts of added Na2O where 0-1 wt is preferred.

A sample of the X-based zeolites of the present invention was found to have a surface area BET (m2/g) of 580.0, a t-plot micropore area (m2/g) of 562.8, a BJH SA of pores from 17-3000 Ang (m2/g) of 24.1. Pore volume was found to be TPV N2 (cc/g) of 0.351, t-Plot Micropore Volume (cc/g) 0.289 and a BJH PV of pores from 17-3000 Ang (cc/g) of 0.066. The enhanced microporosity allows better accessibility to higher cation density. A feed that is being treated may have the composition shown in Table 1.

TABLE 1

|  | % vol | Ppmv |
| --- | --- | --- |
| C3 | 0.7 |  |
| C4 | 97.8 |  |
| C5+ | 1.5 |  |
| C6+ |  | 35 |
| C3= |  | 50 |
| C4= |  | 3000 |
| Ethyl Mercaptan |  | 1-20 |
| Dimethyl sulfide |  | 5-50 |
| Methyl Ethyl Sulfide |  | 5-10 |
| Acetone |  | 10-35 |
| Isopropyl Alcohol |  | 1-10 |

Figure 3A:
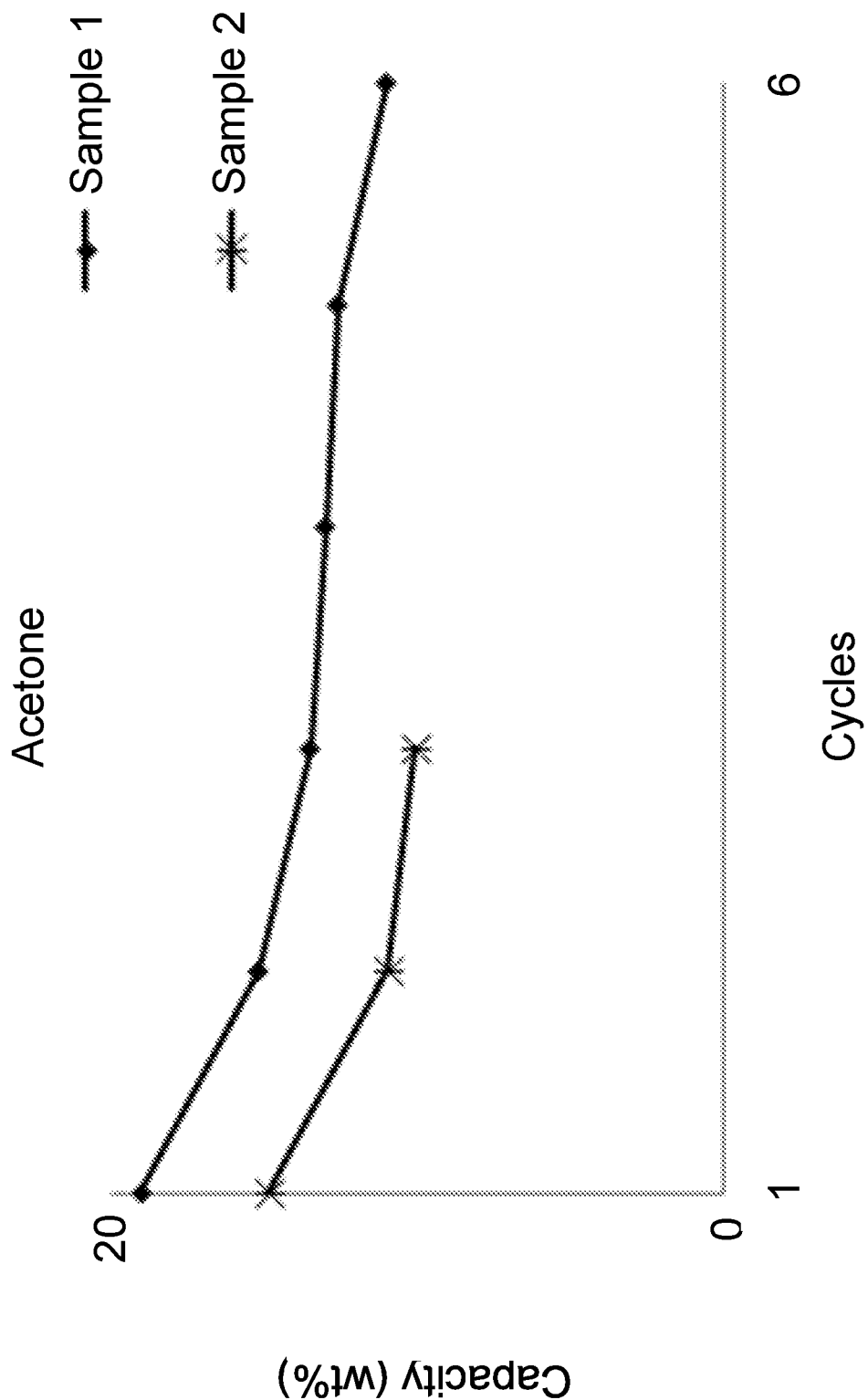
FIG. 3A shows an acetone regenerability curve demonstrating higher capacity and better regenerability using new adsorbent.
Figure 3B:
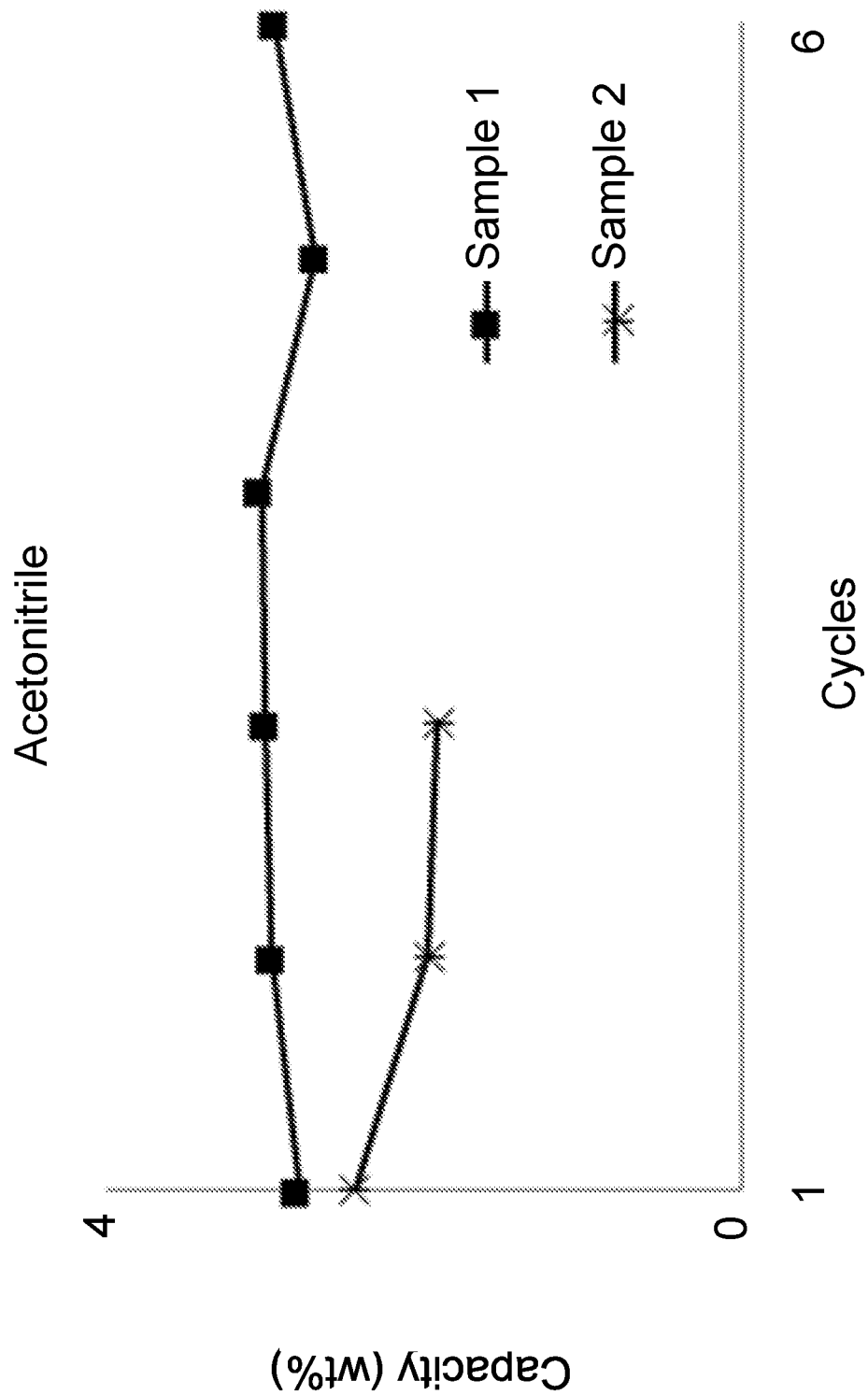
FIG. 3B shows acetonitrile regenerability curve demonstrating higher capacity and better regenerability using new adsorbent.

The adsorbents of the present invention were found to have a higher capacity that was sustained after multiple regeneration cycles when compared to prior art adsorbents such as the current 13× zeolite that has about silica/alumina ratio of about 2.5 (Sample 2) as shown in FIGS. 3A-3C. The breakthrough adsorption test run conditions to generate data in FIGS. 3A-3C is shown below in Table 2.

Figure 4:
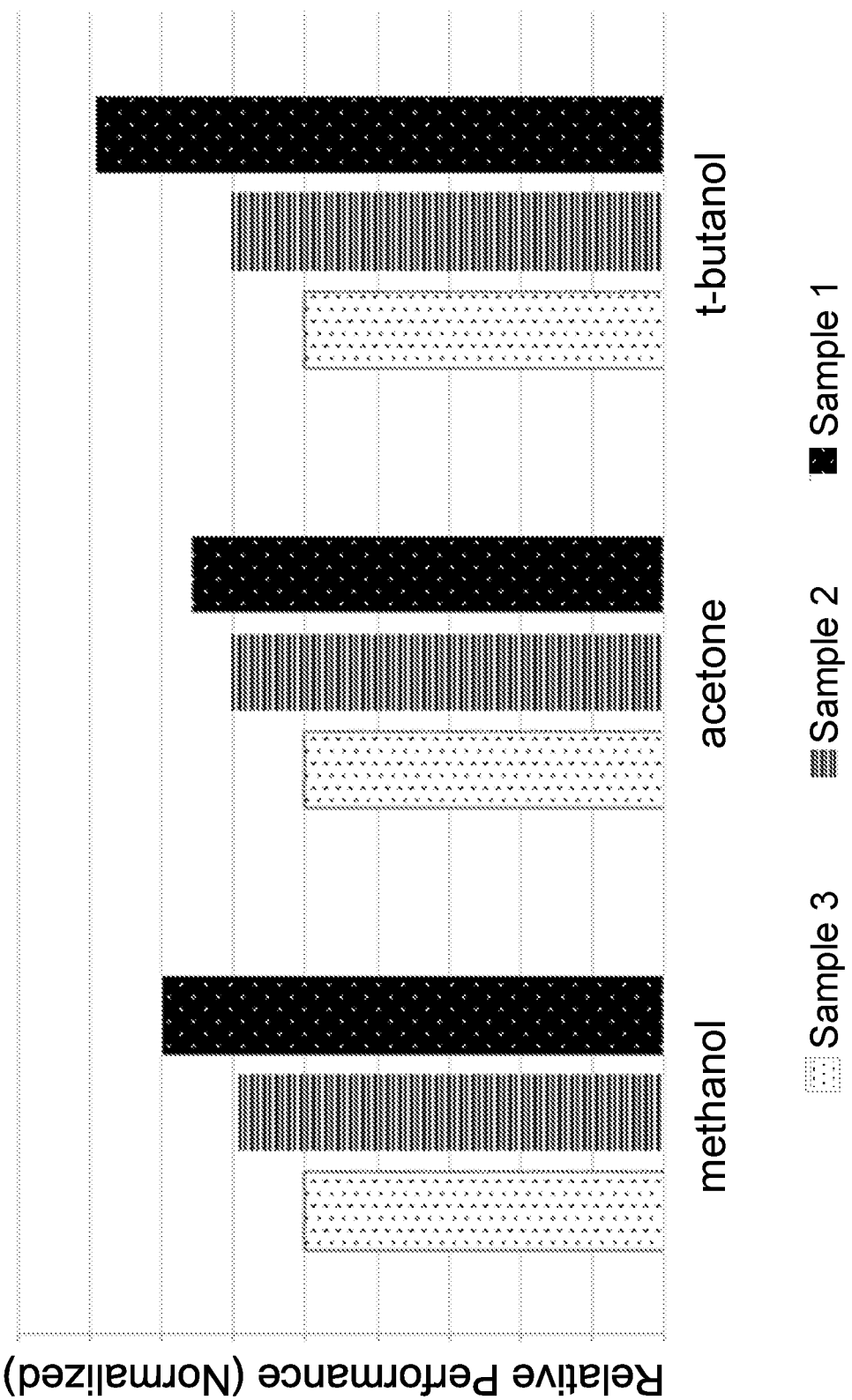
FIG. 4 compares relative performance of samples based on dynamic lab scale testing with a C4 feed.

These adsorbents exhibited higher microporosity, higher microporosity and a higher zeolite content. In addition, the adsorbents of the present invention were found to result in lower olefin oligomerization reactivity by Na doping when measured in an isobutylene reactivity test. The relative performance of new adsorbent Sample 1 in terms of capacity enhancement is shown in FIG. 4.

Example 1

Adsorbent sample were formed in an extruder with 85% 2.1× zeolite/bound with clay binder premixed with various amounts of sodium acetate resulting in 0-5 wt % Na2O after drying and calcination. Adsorbent samples (0.5 gram) were loaded to a micro-reactor and pre-treated under nitrogen flow at 250° C. for 4 hours to activate. The samples were then cooled to 65° C. under continuous nitrogen flow. An olefin containing C4 hydrocarbon mix prepared by pre-mixing the desired contaminants including acetone, acetaldehyde, acetonitrile, dimethyl sulfide, methanol, and t-butanol. The C4 mix stream was introduced to the reactor at a WHSV of 3 hr-1 at 75 psig pressure. An online GC analyzer monitored the reactor effluent stream for the contaminant composition. When the adsorbent was saturated with the contaminants of interest, regeneration was performed under nitrogen flow at 275° C. and the process was repeated. The breakthrough adsorption curves were derived and cyclic capacity after a given number of cycles and compared. FIG. 2 shows the cyclic capacity for acetone of 2.1× zeolite/bound with clay binder samples which were premixed with various amounts of sodium acetate resulting in 0-5 wt % Na2O after drying and calcination. Data shows the highest capacity is achieved from 0-1 wt % Na2O content.

Example 2

Two samples were prepared for testing through Nauta forming, drying and calcination. Sample 1: 90% 2.1×/clay binder/Sodium salt of polyacrylic acid and Sample 2: 88% 2.5×/clay binder/Sodium salt of polyacrylic acid. Each adsorbent sample was tested individually in a flowthrough test. Adsorbent sample (10 grams) was loaded to a reactor and pre-treated under nitrogen flow (2000 sccm) at 288° C. for 4 hours to activate. The sample was then cooled to 40° C. under continuous nitrogen flow (2000 sccm). An olefin containing C4 hydrocarbon mix was pre-mixed with the desired contaminants including acetone, acetaldehyde, acetonitrile, dimethyl sulfide, ethyl mercaptan, methanol, and/or t-butanol. The C4 mix stream was introduced to the reactor at an LHSV of 8 hr-1 at 200 psig pressure. An online GC analyzer monitored the reactor effluent stream for the contaminant composition. When the adsorbent was saturated with contaminants of interest, regeneration was performed under nitrogen flow (2000 sccm) at 288° C. and the cooling and adsorption testing were repeated in multiple cycles. The breakthrough adsorption curves were derived and regenerable capacity curve shown in FIG. 3A to FIG. 3C using Sample 1 and 2. FIG. 3A to FIG. 3C showed cyclic capacity enhancement for Sample 1 from 30-60% for various contaminants with improved regenerability. FIG. 3A shows capacity for acetone, FIG. 3B shows capacity for acetonitrile and FIG. 3C shows capacity for dimethyl sulfide, all in wt %. FIG. 4 provides a comparison of the normalized relative performance of the present invention as Sample 1 with methanol, acetone and t-butanol that is based on dynamic lab scale testing with a C4 feed containing 2000 ppm MAPD & 1% isobutylene. The lab feed and contaminants used for these examples is shown in Table 2.

TABLE 2

|  | % wt | ppmw |
|---|---|---|
| Isobutane | 37 | |
| n-Butane | 12 | |
| Isobutene | 24 | |
| 1-Butene | 15 | |
| 2-Butene (cis/trans) | 11.8 | |
| Isoprene (2 Me-1,3 C4==) | 0.2 | |
| Acetone | | 500 |
| Ethyl Mercaptan | | 20 |
| Dimethyl Sulfide | | 20 |
| Acetonitrile | | 50 |
| Acetaldehyde | | 60 |

Specific Embodiments

While the following is described in conjunction with specific embodiments, it will be understood that this description is intended to illustrate and not limit the scope of the preceding description and the appended claims.

A first embodiment of the invention is a process for removing contaminants from olefin containing $C_4$ streams comprising contacting the olefin containing $C_4$ streams with an X based zeolite adsorbent comprising >88% X zeolite at a $SiO_2/Al_2O_3$ ratio of less than 2.5 and an alkali metal salt present in excess of an amount required to achieve full exchange of cation sites on the X based zeolite wherein a resulting alkali oxide on a volatile free basis is less than 1% (by mass) of the X based adsorbent. An embodiment of the invention is one, any or all of prior embodiments in this paragraph up through the first embodiment in this paragraph wherein the contaminants are selected from the group consisting of sulfur, oxygenate, and nitrogen based contaminants. An embodiment of the invention is one, any or all of prior embodiments in this paragraph up through the first embodiment in this paragraph wherein the X based zeolite adsorbent exhibits a maximum on a log differential specific intrusion volume as measured by Hg porosimetry at a pore diameter of greater than 3000 Angstroms. An embodiment of the invention is one, any or all of prior embodiments in this paragraph up through the first embodiment in this paragraph wherein the X based zeolite adsorbent exhibits a maximum on the log differential specific intrusion volume as measured by Hg Porosimetry at a pore diameter between 3000 and 9000 Angstroms. An embodiment of the invention is one, any or all of prior embodiments in this paragraph up through the first embodiment in this paragraph wherein the X based zeolite adsorbent exhibits a maximum on the log differential specific intrusion volume as measured by Hg porosimetry at a pore diameter between 3000 and 6000 Angstroms. An embodiment of the invention is one, any or all of prior embodiments in this paragraph up through the first embodiment in this paragraph operated at a LHSV from 1-15 hr$^{-1}$, adsorption temperature of 15-70° C. and a pressure of 100-550 psig. An embodiment of the invention is one, any or all of prior embodiments in this paragraph up through the first embodiment in this paragraph wherein the X based zeolite adsorbent is dried in two drying stages comprising a first zone of about 204° C. (400° F.) and a second zone of about 343° C. (650° F.). An embodiment of the invention is one, any or all of prior embodiments in this paragraph up through the first embodiment in this paragraph wherein the X based zeolite adsorbent is dried in three drying stages comprising a first zone of about 385° C. (725° F.), a second zone of about 538° C. (1000° F.). and a third zone of about 576° C. (1070° F.). An embodiment of the invention is one, any or all of prior embodiments in this paragraph up through the first embodiment in this paragraph wherein the X based zeolite adsorbent further comprises a binder. An embodiment of the invention is one, any or all of prior embodiments in this paragraph up through the first embodiment in this paragraph wherein the sulfur contaminant is selected from the group consisting of mercaptans, disulfides, sulfides and mixtures thereof. An embodiment of the invention is one, any or all of prior embodiments in this paragraph up through the first embodiment in this paragraph wherein the oxygenate contaminant is selected from the group consisting of alcohols, ethers, peroxides, carbonyl compounds and mixtures thereof. An embodiment of the invention is one, any or all of prior embodiments in this paragraph up through the first embodiment in this paragraph wherein the nitrogen contaminant is selected from the group consisting of nitriles, amines and mixtures thereof. An embodiment of the invention is one, any or all of prior embodiments in this paragraph up through the first embodiment in this paragraph wherein the $SiO_2/Al_2O_3$ ratio is about 2.1. An embodiment of the invention is one, any or all of prior embodiments in this paragraph up through the first embodiment in this paragraph wherein the alkali metal salt is selected from the group consisting of sodium, potassium, rubidium, cesium salts of acetate, carbonate, carboxylate and polyacrylic acid. An embodiment of the invention is one, any or all of prior embodiments in this paragraph up through the first embodiment in this paragraph wherein the alkali metal salt is selected from the group consisting of sodium salts of acetate, carbonates, carboxylates and polyacrylic acid. An embodiment of the invention is one, any or all of prior embodiments in this paragraph up through the first embodiment in this paragraph wherein the X based zeolite adsorbent has a micropore volume of greater than 0.28 g/cc measured by a t-plot method. An embodiment of the invention is one, any or all of prior embodiments in this paragraph up through the first embodiment in this paragraph wherein the X based zeolite adsorbent has a micropore volume between 0.28 to 0.30 g/cc as measured by the t-plot method. An embodiment of the invention is one, any or all of prior embodiments in this paragraph up through the first embodiment in this paragraph wherein the X based zeolite is regenerated in a thermal swing adsorption process at a temperature from about 250° C. and 300° C. in a heated gas. An embodiment of the invention is one, any or all of prior embodiments in this paragraph up through the first embodiment in this paragraph wherein less than 1 wppm of the contaminants remain in the olefin containing $C_4$ streams after contact with the X based zeolite. An embodiment of the invention is one, any or all of prior embodiments in this paragraph up through the first embodiment in this paragraph wherein the X based zeolite after use to remove contaminants has a reduced level of coke buildup.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. A process for removing contaminants from olefin containing $C_4$ streams comprising contacting said olefin containing $C_4$ streams with an X based zeolite adsorbent wherein the X based zeolite adsorbent comprises:
>88% alkali metal cation form of X zeolite having a $SiO_2/Al_2O_3$ ratio of less than 2.5, wherein Al content has been fully charge balanced by an addition of the alkali metal cation: and
less than 1% (by mass) additional alkali oxide on a volatile free basis.

2. The process of claim 1 wherein said contaminants are selected from the group consisting of sulfur, oxygenate, and nitrogen based contaminants.

3. The process of claim 1 wherein the X based zeolite adsorbent exhibits a maximum on a log differential specific intrusion volume as measured by Hg porosimetry at a pore diameter of greater than 3000 Angstroms.

4. The process of claim 1 wherein the X based zeolite adsorbent exhibits a maximum on the log differential specific intrusion volume as measured by Hg Porosimetry at a pore diameter between 3000 and 9000 Angstroms.

5. The process of claim 1 wherein the X based zeolite adsorbent exhibits a maximum on the log differential specific intrusion volume as measured by Hg porosimetry at a pore diameter between 3000 and 6000 Angstroms.

6. The process of claim 1 operated at a LHSV from 1-15 $hr^{-1}$, adsorption temperature of 15-70° C. and a pressure of 100-550 psig.

7. The process of claim 1 wherein the X based zeolite adsorbent is prepared by:
mixing the X zeolite with an alkali metal salt; and
drying the mixture in two drying stages comprising a first zone of about 204° C. (400° F.) and a second zone of about 343° C. (650° F.).

8. The process of claim 1 wherein the X based zeolite adsorbent is prepared by:
mixing the X zeolite with an alkali metal salt; and
drying the mixture in three drying stages comprising a first zone of about 385° C. (725° F.), a second zone of about 538° C. (1000° F.), and a third zone of about 576° C. (1070° F.).

9. The process of claim 1 wherein the X based zeolite adsorbent further comprises a binder.

10. The process of claim 2 wherein the sulfur contaminant is selected from the group consisting of mercaptans, disulfides, sulfides and mixtures thereof.

11. The process of claim 2 wherein the oxygenate contaminant is selected from the group consisting of alcohols, ethers, peroxides, carbonyl compounds and mixtures thereof.

12. The process of claim 2 wherein the nitrogen contaminant is selected from the group consisting of nitriles, amines and mixtures thereof.

13. The process of claim 1 wherein the $SiO_2/Al2O_3$ ratio is about 2.1.

14. The process of claim 7 wherein the alkali metal salt is selected from the group consisting of sodium, potassium, rubidium, cesium salts of acetate, carbonate, carboxylate and polyacrylic acid.

15. The process of claim 14 wherein the alkali metal salt is selected from the group consisting of sodium salts of acetate, carbonates, carboxylates and polyacrylic acid.

16. The process of claim 1 wherein the X based zeolite adsorbent has a micropore volume of greater than 0.28 cc/g measured by a t-plot method.

17. The process of claim 16 wherein the X based zeolite adsorbent has a micropore volume between 0.28 to 0.30 cc/g as measured by the t-plot method.

18. The process of claim 1 further comprising:
regenerating the X based zeolite adsorbent in a thermal swing adsorption process at a temperature from about 250° C. and 300° C. in a heated gas after contacting said olefin containing $C_4$ streams with the X based zeolite adsorbent.

19. The process of claim 1 wherein less than 1 wppm of said contaminants remain in said olefin containing $C_4$ streams after contact with the X based zeolite adsorbent.

20. The process of claim 1 wherein the X based zeolite adsorbent after use to remove contaminants has a reduced level of coke buildup compared to a zeolite adsorbent without additional alkali oxide.

* * * * *